US011141220B2

(12) United States Patent
Mortier et al.

(10) Patent No.: US 11,141,220 B2
(45) Date of Patent: Oct. 12, 2021

(54) METHOD AND SYSTEM FOR DETERMINING A RISK OF CARDIAC CONDUCTION ABNORMALITIES

(71) Applicant: FEops NV, Ghent (BE)

(72) Inventors: Peter Eddy J Mortier, Ghent (BE); Gianluca De Santis, Ghent (BE); Matthieu Robert Anna Firmin De Beule, Ghent (BE)

(73) Assignee: FEops NV, Ghent (BE)

( * ) Notice: Subject to any disclaimer, the term of this patent is extended or adjusted under 35 U.S.C. 154(b) by 1016 days.

(21) Appl. No.: 15/570,976

(22) PCT Filed: Apr. 29, 2016

(86) PCT No.: PCT/EP2016/059688
§ 371 (c)(1),
(2) Date: Oct. 31, 2017

(87) PCT Pub. No.: WO2016/177647
PCT Pub. Date: Nov. 10, 2016

(65) Prior Publication Data
US 2018/0289422 A1 Oct. 11, 2018

(30) Foreign Application Priority Data

May 1, 2015 (EP) ..................................... 15166130

(51) Int. Cl.
| A61B 34/10 | (2016.01) |
| G16H 50/30 | (2018.01) |
| G16H 50/50 | (2018.01) |
| G16H 50/20 | (2018.01) |
| A61F 2/24 | (2006.01) |
| G06T 7/00 | (2017.01) |
| G06F 30/23 | (2020.01) |
| G06T 17/20 | (2006.01) |
| G06T 19/00 | (2011.01) |
| A61B 17/00 | (2006.01) |

(52) U.S. Cl.
CPC ............ *A61B 34/10* (2016.02); *A61F 2/2427* (2013.01); *G06T 7/0012* (2013.01); *G06T 17/20* (2013.01); *G06T 19/00* (2013.01); *G16H 50/20* (2018.01); *G16H 50/30* (2018.01); *G16H 50/50* (2018.01); *A61B 2017/00243* (2013.01); *A61B 2017/00783* (2013.01); *A61B 2034/104* (2016.02); *A61B 2034/105* (2016.02); *G06F 30/23* (2020.01); *G06T 2207/30048* (2013.01); *G06T 2210/41* (2013.01)

(58) Field of Classification Search
None
See application file for complete search history.

(56) References Cited

U.S. PATENT DOCUMENTS

| 8,682,626 B2 | 3/2014 | Ionasec et al. |
| 2005/0043609 A1 | 2/2005 | Murphy et al. |
| 2007/0135707 A1 | 6/2007 | Redel et al. |
| 2011/0153286 A1 | 6/2011 | Zaeuner et al. |
| 2015/0051884 A1 | 2/2015 | Grady et al. |
| 2015/0112659 A1 | 4/2015 | Mortier |
| 2015/0370995 A1 | 12/2015 | Wakai |
| 2016/0166332 A1 | 6/2016 | Wang et al. |
| 2019/0357981 A1 | 11/2019 | Mortier et al. |

FOREIGN PATENT DOCUMENTS

| DE | 102012205504 A1 | 10/2013 |
| WO | WO-2013156546 A2 | 10/2013 |
| WO | 2013171039 A1 | 11/2013 |
| WO | 2014009294 A1 | 1/2014 |
| WO | WO-2016038169 A1 | 3/2016 |
| WO | WO-2016177647 A1 | 11/2016 |
| WO | WO-2018141927 A1 | 8/2018 |
| WO | WO-2019179793 A1 | 9/2019 |
| WO | WO-2020182651 A1 | 9/2020 |

OTHER PUBLICATIONS

Ghadimi et al. (Journal of Cardiothoracic and Vascular Anesthesia (2013) vol. 27:1414-1420).*
Steinberg et al. (The America Heart Journal (2012) vol. 164:664-671).*
Antiga, et al., An Image-Based Modeling Framework for Patient-Specific Computational Hemodynamics, Medical & Biological Engineering & Computing, vol. 46:1097-1112 (2008).
Auricchio, et al., Carotid Artery Stenting Simulation: From Patient-Specific Images to Finite Element Analysis, Medical Engineering and Physics, vol. 33:281-289 (2011).
Capelli et al., "Patient-Specific Simulations of Transcatheter Aortic Valve Stent Implantation," Med. Medical & Biological Engineering & Computing, Jan. 29, 2012, 50:183-192 (2012).
De Santis, et al., Patient-Specific Computational Fluid Dynamics: Structured Mesh Generation from Coronary Angiography, Medical & Biological Engineering & Computing, vol. 48:371-380 (2010).

(Continued)

*Primary Examiner* — Lori A. Clow
(74) *Attorney, Agent, or Firm* — Eversheds Sutherland (US) LLP; Christopher C. Bolten; Nicola A. Pisano

(57) ABSTRACT

A method and system for determining a measure of a risk of a patient developing cardiac conduction abnormalities as a result of transcatheter cardiac treatment. The method includes providing a patient-specific anatomical model representing cardiac region and an implant model representing a finite element representation of a cardiac implant. The method includes virtually placing said implant model into said patient-specific anatomical model. A measure of mechanical interaction between the implant model and the patient-specific anatomical model is determined and a measure of risk of the patient developing cardiac conduction abnormalities is determined on the basis of the determined mechanical interaction.

20 Claims, 7 Drawing Sheets

(56) References Cited

OTHER PUBLICATIONS

European Search Report dated Jul. 11, 2017 in EP Patent Appl. Serial No. 17154648.4.
European Search Report dated Oct. 2, 2018 in EP Patent Appl. Serial No. 18163655.6.
Grbic, et al., Complete Valvular Heart Apparatus Model from 4D Cardiac CT, Field Programmable Logic and Application, vol. 6361:218-226 (2010).
International Search Report and Written Opinion dated Jul. 15, 2016 in Int'l PCT Patent Application Serial No. PCT/EP2016/059688.
International Search Report and Written Opinion dated Jul. 30, 2013 in Int'l PCT Patent Application Serial No. PCT/EP2013/058392.
International Search Report and Written Opinion dated Jun. 4, 2018 in Int'l PCT Patent Application Serial No. PCT/EP2018/052701.
International Search Report and Written Opinion dated May 31, 2019 in Int'l PCT Patent Application Serial No. PCT/EP2019/055907.
Lenoir, et al., Physics-Based Models for Catheter, Guidewire and Stent Simulation, Medicine Meets Virtual Reality, 14:305-310 (2006).
Morganti, et al., Simulation of Transcatheter Aortic Valve Implantation through Patient-Specific Finite Element Analysis: Two Clinical Cases, Journal of Biomechanics, 47:2547-2555 (2014).
Mortier, et al., A Novel Simulation Strategy for Stent Insertion and Deployment in Curved Coronary Bifurcations: Comparison of Three Drug-Eluting Stents, Annals of Biomedical Engineering, vol. 38(1):88-99 (Jan. 2010).
Russ, et al., Simulation of Transcatheter Aortic Valve Implantation Under Consideration of Leaflet Calcification, 35th Annual International Conference of the IEEE EMBS, Osaka, Japan, pp. 711-714 (Jul. 2013).
Schneider, et al., Modeling Mitral Valve Leaflets from Three-Dimensional Ultrasound, Field Programmable Logic and Application, vol. 6666:215-222 (2011).
Sun, et al., Simulated Elliptical Bioprosthetic Valve Deformation: Implications for Asymmetric Transcatheter Valve Deployment, Journal of Biomechanics, 43:3085-3090 (2010).
Viscardi, et al., Comparative Finite Element Model Analysis of Ascending Aortic Flow in Bicuspid and Tricuspid Aortic Valve, Artificial Organs, vol. 34:1114-1120 (2010).
Vy, et al., Review of Patient-Specific Simulations of Transcatheter Aortic Valve Implantation, HAL Archives, https:/hal-univ-rennes1.archives-ouvertes.fr/hal-01196296, pp. 1-33, (Sep. 9, 2015).
U.S. Appl. No. 14/399,781, filed Nov. 7, 2014.
U.S. Appl. No. 16/482,509, filed Jul. 31, 2019.
U.S. Appl. No. 16/987,794, filed Aug. 7, 2020.
U.S. Appl. No. 17/003,653, filed Aug. 26, 2020.
Wang et al., "Patient-Specific Modeling of Biomechanical Interaction in Transcatheter Aortic Valve Deployment", Journal of Biomechanics, vol. 45, pp. 1965-1971; 2012.
Rocatello et al., "Patient-Specific Computer Simulation to Elucidate the Role of Contact Pressure in the Development of New Conduction Abnormalities After Catheter-Based Implantation of a Self-Expanding Aortic Valve", Circulation Cardiovascular Interventions, pp. 1-9; 2018.
Basri, et al., *The Hemodynamic Effects of Paravalvular Leakage Using Fluid Structure Interaction; Transcatheter Aortic Valve Implantation Patient*, Journal of Medical Imaging and Health Informatics, 6(5):1513-1518 (2016).
Extended EP Search Report dated Sep. 14, 2019 in EP Patent Appl. Serial No. 19161587.7.
International Search Report & Written Opinion dated Jun. 5, 2020 in Int'l PCT Patent Appl. Serial No. PCT/EP2020/056000.
Sirois, et al., *Hemodynamic Impact of Transcatheter Aortic Valve Deployment Configuration*, Journal of Medical Devices, 7(4):040922.1-040922.2 (Dec. 2013), 2 pages.

* cited by examiner

METHOD AND SYSTEM FOR DETERMINING A RISK OF CARDIAC CONDUCTION ABNORMALITIES

This application is the U.S. National Phase of, and Applicants claim priority from, International Patent Application Number PCT/EP2016/059688 filed 29 Apr. 2016, which claims priority from EP 15166130.3 filed 1 May 2015, each of which is incorporated herein by reference.

FIELD OF THE INVENTION

The present invention relates to the field of pre-operative planning of transcatheter structural heart interventions, e.g. valve treatment, such as valve implantation and/or repair. More in particular, the invention relates to pre-operative prediction of the risk a patient developing cardiac conduction abnormalities as a result of transcatheter valve treatment.

BACKGROUND TO THE INVENTION

The left ventricle of the heart pumps the blood to the aorta through the aortic valve. Aortic (valve) stenosis is a pathology occurring when the aortic valve does not open fully because the leaflets calcify, thicken and stiffen and, as a result, the blood flow going from the heart to the systemic circulation decreases. Aortic stenosis manifests itself in elderly people, with a prevalence going from 1.3% in over 65 and 4% in over 85 year old people. Currently it is the most common valvular heart disease in the Western world and its prevalence is increasing with the aging population.

The standard treatment for an aortic stenosis is the Surgical Aortic Valve Replacement (SAVR) aiming at reproducing the correct function of the native valve with an implanted valve. This invasive procedure requires total anesthesia, sternotomy (open-heart surgery) and cardiopulmonary bypass (the blood is pumped and oxygenated using an external machine), and is associated with about 6% in-hospital mortality for over 65 year old patients. Moreover, at least one-third of the patients with severe aortic stenosis are denied valve surgery as the risks associated with surgery are too high.

Trans-catheter aortic valve implantation (TAVI) or trans-catheter aortic valve replacement (TAVR) is a minimally-invasive procedure for treating aortic stenosis: (1) the valve (e.g. a bioprosthetic valve made of porcine pericardium sutured on a metal stent) is crimped inside a catheter, (2) the catheter is inserted, for example, in the femoral artery, (3) pushed upstream along the aorta up to the aortic annulus and (4) the new valve is deployed within the diseased native valve. TAVI has the potential of treating high-risk patients and replacing the SAVR with a minimally-invasive intervention (no need for open-heart surgery or cardiopulmonary bypass) which can be performed in e.g. about 80 minutes. Main TAVI complications are vascular injury, stroke, cardiac injury (heart block, coronary obstruction, cardiac perforation), aortic regurgitation, cardiac conduction abnormalities and valve misplacement. Accurate pre operative planning is crucial to select the optimal device size and to anticipate potential difficulties.

Undersizing of a valve implant may lead to paravalvular aortic regurgitation, while oversizing may result in a rupture of the aortic annulus or in a suboptimal functional behavior of the implant. Currently available planning tools (Philips, Siemens, Pie Medical, Paeion) provide insights into the patient anatomy and can, for example, be used to determine the size of the aortic annulus, or to measure the distance between the valve plane and the coronary ostia. A problem with these tools is that they do not provide preoperative insights into the interaction between a certain implant device and the specific patient anatomy, and can thus not be used to predict complications such as regurgitation. Such insights are extremely valuable for interventional cardiologists.

Another problem is that is difficult to reconstruct native leaflets from e.g. CT images. In the currently deployed methods, an incomplete leaflet image is obtained, comprising gaps whereby the gaps represent a lack of data.

Document US 2011/0153286 A1 discloses a method and system for virtual percutaneous valve implantation. In one embodiment of the application a patient-specific anatomical model of a heart valve is estimated based on 3D cardiac medical image data. An implant model representing a valve implant is virtually deployed into the patient-specific anatomical model of the heart valve. A library of implant models, each modeling geometrical properties of a corresponding valve implant, can be maintained. The implant models maintained in the library can be virtually deployed into the patient specific anatomical model of the heart valve to select one of the implant models for use in a percutaneous valve implantation procedure.

US 2011/0153286 A1 does not provide a prediction of the mechanical behavior and interaction of the patient-specific aortic root, ascending aorta and aortic valve leaflets with the deployment of a valve implant. Said document also does not account for calcification of aortic valve leaflets. Neither does it provide a means to study the hemodynamic performance of an implant deployed in the aortic valve. Balloon-expandable devices whose deployment is based on permanent plastic deformations of the metal cannot be modeled. There is a need for more precise valve sizing and positioning. Problem is that the aortic annulus is not circular, that the aortic annulus may deform and that calcium deposits may deform a valve frame. Another problem is that the aortic root visualized with Computed Tomography (CT) imaging changes in shape and size after TAVI. Also the geometry of the stent frame of the transcatheter aortic valve (TAV) is affected by the stiffness of the aortic root, by the presence of stiff calcified regions and by the exact device position.

Sub-optimal treatment planning can have two socio-economic effects. On the one hand this gives higher costs for the health system. If the incorrect device/size of the TAV is chosen, the first TAVI procedure may fail and additional treatments, including a second TAVI procedure (valve-in-valve), SAVR, or rehospitalization may be necessary, with a considerable increase of the costs per patient. As a reference, one single TAVI procedure costs about 40 k Euro and the stented valve itself costs about 20 k Euro. On the other hand this leads to a lower prognosis. Sub-optimal treatment planning may result in peri-procedural complications, which affect both the life quality and the life expectancy of the patient. An oversized valve may rupture the annulus or dissect the aorta whereas an undersized valve may dislodge and migrate or can induce paravalvular regurgitation.

In WO2013/171039 A1 the present inventors described a solution to overcome at least part of the above mentioned disadvantages. WO2013/171039 A1 provides an improved method for preoperative insights into the interaction of an implant device and specific patient anatomy, for better prediction of complications, such as regurgitation, for better prediction of the hemodynamic performance of an implant deployed in an aortic valve, and for better patient selection and stratification. Also WO2013/171039 A1 provides a web-based pre-operative planning service for TAVI using computer simulations that predict stent frame deformation and incomplete frame apposition, allowing to assess the risk on regurgitation and other complications such as coronary obstruction and conduction abnormalities prior to the intervention.

Recent studies state that TAVI can induce cardiac conduction abnormalities, the most frequent being left bundle-branch block (LBBB). Here is for instance referred to "Left Bundle-Branch Block Induced by Transcatheter Aortic Valve Implantation Increases Risk of Death", by Houthuizen et al., 2012. Therefore, there is a need for pre-operative conduction problem risk analysis.

SUMMARY OF THE INVENTION

The invention relates to a method for determining a measure of a risk of a patient developing cardiac conduction abnormalities and/or disorders, such as left bundle-branch block (LBBB), as a result of transcatheter structural heart intervention, such a transcatheter cardiac valve treatment. The treatment may be trans-catheter valve implantation/replacement or trans-catheter valve repair. The transcatheter cardiac valve may e.g. be a transcatheter aortic or mitral valve. The method includes providing a patient-specific anatomical model representing a patient-specific cardiac region, such as a patient-specific cardiac valve region. The patient-specific anatomical model may represent a patient-specific aorta. The patient-specific anatomical model comprises a finite element mesh. The method includes providing an implant model representing a finite element representation of a cardiac implant, such as a cardiac valve implant, e.g. an aortic valve implant. The implant model is virtually, e.g. in silico, placed, e.g. deployed, into the patient-specific anatomical model. From the virtually placed implant model in the patient-specific anatomical model, a measure of a mechanical interaction between the implant model and the patient-specific anatomical model is determined. The determined measure of the mechanical interaction represents a calculation of a mechanical interaction between the cardiac implant and the cardiac region of the patient. On the basis of the determined mechanical interaction, a measure is determined of the risk of the patient developing cardiac conduction abnormalities and/or disorders. On the basis of the determined mechanical interaction, a measure is determined, the measure being a predictor of cardiac conduction abnormalities and/or disorders in a patient if an actual implant corresponding to the implant model were actually implanted in the anatomical region of the patient corresponding to the patient-specific anatomical model.

It will be appreciated that the method includes computer implemented steps. It will be appreciated that all above mentioned steps can be computer implemented steps.

Determining the mechanical interaction between a cardiac valve implant and a cardiac valve region of the patient is an important example of the present invention. Nevertheless, the invention can also be applied to other implants, such as stents. Although below is referred in particular to a cardiac valve implant and a cardiac valve region of the patient, it will be appreciated that the features and advantages also apply to other implants for the heart. Therefore, for the purpose of understanding the invention where below is referred to a cardiac valve implant and cardiac valve region this similarly holds for other cardiac implants and/or other cardiac regions.

The measure of the mechanical interaction may include a measure of contact pressure between the cardiac valve implant and the cardiac valve region of the patient. The determined contact pressure represents a calculation of a pressure between the cardiac valve implant and the cardiac valve region of the patient. On the basis of the determined contact pressure, a measure can be determined of the risk of the patient developing cardiac conduction abnormalities and/or disorders. Alternatively, or additionally, the measure of the mechanical interaction may include a measure of strain in the tissue in the cardiac valve region of the patient due to the presence of the cardiac valve implant. The determined strain represents a calculation of a strain in the tissue in the cardiac valve region of the patient. On the basis of the determined strain, a measure can be determined of the risk of the patient developing cardiac conduction abnormalities and/or disorders.

It will be appreciated that this method provides the advantage that the measure of the risk of the patient developing cardiac conduction abnormalities and/or disorders, such as left bundle-branch block (LBBB), as a result of transcatheter treatment of the cardiac valve can be predicted preoperatively. Hence, it is possible to predict how likely the TAVI or TAVR procedure will result in cardiac conduction problems. Conduction disturbances can be split into many different categories. TAVI may cause left bundle branch block (LBBB), or AV (atrio ventricular) block. A high degree AV block often requires a pacemaker, while this is not so often the case for LBBB. The method allows to predict LBBB and/or AV block by investigating the relevant region of interest. As a result, it may be predicted whether the TAVI or TAVR procedure ultimately may necessitate the implantation of a cardiac pacemaker. Alternatively, the method allows to predict the risk of conduction problems for a plurality of different transcatheter cardiac valves. This, in turn, may allow to select the optimum transcatheter cardiac valve for the specific patient.

Optionally, determining the measure of the mechanical interaction includes determining a measure of a surface area within which the determined mechanical interaction exceeds a predetermined threshold. For example, determining the measure of the contact pressure includes determining a measure of a surface area within which the determined pressure exceeds a predetermined threshold, i.e. a surface area within which the determined pressure is not lower than the predetermined threshold. The risk of the patient developing cardiac conduction abnormalities and/or disorders can be quantified by determining a surface area on the patient-specific anatomical model where the contact pressure exerted by the implant model onto the patient-specific anatomical model exceeds a predetermined threshold. A larger surface area can indicate a higher risk. It will be appreciated that an appropriate threshold level can be determined by calibration. Calibration may require determining the surface area in pre-operative anatomical models of a plurality of patents, and determining post-operatively whether or not these patients develop cardiac conduction abnormalities and/or problems. Alternatively, or additionally, determining the measure of the strain can include determining a measure of a surface area within which the determined strain exceeds a predetermined threshold, i.e. a surface area within which the determined strain is not lower than the predetermined threshold.

Optionally, determining the measure of the contact pressure includes determining a total contact force. The total contact force can be the determined contact pressure integrated over the surface area of contact. A larger total force can indicate a higher risk.

Optionally, determining the measure of the strain includes determining a total strain. The total strain can be the determined strain integrated over the surface area of contact. A larger total strain can indicate a higher risk.

Optionally, determining the measure of the contact pressure includes determining a peak pressure of the determined pressure. A higher peak pressure can indicate a higher risk.

Optionally, determining the measure of the strain includes determining a peak strain of the determined strain. A higher peak strain can indicate a higher risk.

Optionally, determining the measure of the mechanical interaction includes determining a location in the patient-specific anatomical model where the peak pressure or peak strain occurs. A location of the peak pressure or peak strain can indicate a measure of the risk. A combination of the location of the peak pressure and the value of the peak pressure can indicate a measure of the risk. A combination of the location of the peak strain and the value of the peak strain can indicate a measure of the risk.

Optionally, determining the measure of the contact pressure includes defining a predetermined region of the patient-specific anatomical model, and determining the measure of the contact pressure within that predetermined region. The predetermined region can e.g. be a region under the aortic annulus. The predetermined region can e.g. be a region on the left ventricular outflow tract under the aortic annulus. The predetermined region can e.g. be a region on the left ventricular outflow tract under the aortic annulus between the basal attachment points of the non- and right coronary leaflet. It will be appreciated that a region can be determined by calibration as described above, mutatis mutandis. Similarly, determining the measure of the strain includes defining a predetermined region of the patient-specific anatomical model, and determining the measure of the strain within that predetermined region.

Optionally, determining the measure of the mechanical interaction includes defining a predetermined region of the patient-specific anatomical model, and determining a measure of a surface area within the predetermined region within which the determined pressure or strain exceeds a predetermined threshold.

Optionally, determining the measure of the mechanical interaction includes defining a predetermined region of the patient-specific anatomical model, and determining a total contact force or total strain within the predetermined region. The total contact force in the predetermined region can be the determined contact pressure integrated over the surface area of the predetermined region. A larger total force or strain in the predetermined region can indicate a higher risk.

Optionally, determining the measure of the mechanical interaction includes defining a predetermined region of the patient-specific anatomical model, and determining a peak pressure or peak strain of the determined pressure within the predetermined region. A higher peak pressure or strain can indicate a higher risk.

Optionally, determining the measure of the mechanical interaction includes defining a predetermined region of the patient-specific anatomical model, and determining a location in the patient-specific anatomical model where the peak pressure or peak strain within the predetermined region occurs. A location of the peak pressure or peak strain within the predetermined region can indicate a measure of the risk. A combination of the location of the peak pressure or strain and the value of the peak pressure or strain in the predetermined region can indicate a measure of the risk.

Optionally, determining the measure of the mechanical interaction includes determining an evolution of the mechanical interaction over time during the process of deployment. It is possible to determine the measure of the mechanical interaction at a first moment and at a second moment. The first moment may be prior to the implant model being fully placed into the patient-specific anatomical model. The second moment may be after the implant model has been fully placed into the patient-specific anatomical model. It is also possible to determine the measure of the mechanical interaction at a plurality of first moments. Hence a time evolution of the mechanical interaction during deployment of the implant model can be determined. It has been found that conduction disturbances can also occur during the intervention, e.g. prior to final deployment of a device. This may be related to intermediate forces and/or deformation of tissue. This can be simulated by determining the time evolution, e.g. prior to actual deployment of the implant in the patient.

Optionally, determining the measure of the mechanical interaction may include determining a series of situations of progressing deployment of the implant model into the patient-specific anatomical model. The situations may progressively differ by a predetermined amount or ratio of deployment. The deployment can include insertion of the implant model into the patient-specific anatomical model. The insertion can include travel of a model of a, collapsed, implant along a vessel. The series of situations can include situations of progressively differing positions of insertion up to an intended deployment position. The deployment can include expansion of the implant model in the patient-specific anatomical model. The series of situations can include situations of progressively differing stages of expansion of the implant model. For each of the situations of the series of situations the measure of the mechanical interaction can be determined as described above. Hence, all stages of deployment can be modeled. The processing unit can be arranged to determine the situation of the series of situations in which the determined mechanical interaction is most significant, e.g. highest. The processing unit may be arranged to determine the measure of mechanical interaction in the situation of the series of situations in which the determined mechanical interaction is most significant for predicting conduction problems, e.g. highest. The series of situations may be generated for a plurality of different deployment positions. The processing unit may be arranged to select the optimum deployment position.

It will be appreciated that the risk of the patient developing cardiac conduction abnormalities and/or disorders can be quantified by taking a combination of the determinations mentioned above.

Optionally, the method includes estimating the patient-specific anatomical model on the basis of a, preferably preoperative, cardiovascular 2D or 3D medical image data, such as a CT-scan, an MRI image, echocardiography images or the like.

Optionally, the method includes estimating the patient-specific anatomical model on the basis of anatomical measurements, using for example, a parametric heart model.

Optionally, the method includes estimating a position of the conduction system in the patient-specific anatomical model. It has been found that the inferior margin of the membranous septum is an anatomic surrogate for the location of the His bundle. The inferior margin of the membranous septum can be from cardiovascular 2D or 3D medical image data, such as a CT-scan, an MRI image, echocardiography images or the like. Estimating a position of the conduction system can include identifying three points in the medical image data. A first point (p1) represents the starting point of the inferior margin closest to the non-coronary cusp, A third point (p3) represents the end of the inferior margin closest to the right coronary cusp. A third point (p2) is identified between the first and second points. The three points determine the estimated location of the conduction system.

Optionally, determining the measure of the mechanical interaction includes determining the measure of mechanical interaction at or around the estimated location of the conduction system.

Optionally, the implant model comprises a finite element mesh. Each element of said mesh can be featured by a set of nodes. Adjacent elements of said element can comprise mutually shared nodes with said element. Said element can be featured by material dependent parameters. Each element of said mesh can differ in material dependent parameters from an adjacent element of said element of said mesh.

Optionally, stiffness elements are provided to a plurality of nodes of a mesh of the anatomical model. A stiffness element induces a reacting force on the corresponding node of said mesh, wherein said force is dependent on the displacement of said node or on the distance between said node and a fixed position equal or very close to the initial position of said node.

Optionally, the step of virtually placing the implant model into the patient-specific anatomical model includes a three-dimensional finite element analysis. Hence, deployment of the implant in the patient-specific anatomical model can be simulated in silico in three dimensions.

Optionally, the method includes virtually placing the implant model into the patient-specific anatomical model at a plurality of different locations and determining the measure of the risk of a patient developing cardiac conduction abnormalities for each of the different locations. Hence, it is possible to assess the risk of cardiac conduction abnormalities for the plurality of different locations of the implant. Hence, it is also possible to select the location for the implant associated with the lowest risk of developing cardiac conduction abnormalities. Such selected location can be used in pre-operative planning of a TAVI or TAVR procedure.

Optionally, the step of virtually placing the implant model includes providing a plurality of implant models, each modeling geometrical and/or material properties of a corresponding implant; and virtually deploying each of the implant models into the patient specific anatomical model, and determining the measure of the risk of a patient developing cardiac conduction abnormalities for each of the implant models. Hence, it is possible to assess the risk of cardiac conduction abnormalities for each the plurality of different implant models. Hence, it is also possible to select the implant model associated with the lowest risk of developing cardiac conduction abnormalities. Such selected implant model can be used in pre-operative planning of a TAVI or TAVR procedure. The method can include selecting a cardiac valve implant corresponding to one of the plurality of the implant models for a percutaneous implantation procedure. A cardiac valve implant associated with the selected implant model can be used in a percutaneous implantation procedure to minimize risk of the patient developing cardiac conduction abnormalities.

Optionally, the method includes reporting the measure of the mechanical interaction to a user. The measure of mechanical interaction may e.g. be displayed on a display, printed in hardcopy or the like. It is also possible to report an indication of the risk of the patient developing cardiac conduction abnormalities to the user.

The invention also relates to a system for determining a measure of a risk of a patient developing cardiac conduction abnormalities as a result of transcatheter cardiac valve treatment. The system includes a processor. The processor is arranged for receiving a patient-specific anatomical model representing a patient-specific cardiac valve region. The patient-specific anatomical model can comprise a finite element mesh. The processor is arranged for receiving an implant model representing a finite element representation of a cardiac valve implant. The processor is arranged for virtually placing said implant model into said patient-specific anatomical model. The processor is arranged for determining, from the virtually placed implant model into said patient-specific anatomical model, a measure of a mechanical interaction between the implant model and the patient-specific anatomical model. The processor is arranged for determining a measure of risk of the patient developing cardiac conduction abnormalities on the basis of the determined mechanical interaction. Thus, the system can be used to perform the method as described above.

The invention also relates to a computer program product including computer implementable instructions. The computer program product can be stored on a non-transient data carrier. When implemented by a programmable computer the instructions cause the computer to retrieve a patient-specific anatomical model representing a patient-specific cardiac valve region. The patient-specific anatomical model comprises a finite element mesh. When implemented by a programmable computer the instructions cause the computer to retrieve an implant model representing a finite element representation of a cardiac valve implant. When implemented by a programmable computer the instructions cause the computer to virtually place said implant model into said patient-specific anatomical model. When implemented by a programmable computer the instructions cause the computer to determine, from the virtually placed implant model into said patient-specific anatomical model, a measure of a mechanical interaction between the implant model and the patient-specific anatomical model. When implemented by a programmable computer the instructions cause the computer to determine a measure of risk of the patient developing cardiac conduction abnormalities on the basis of the determined mechanical interaction. Thus, the computer program product can be used to perform the method as described above.

It will be appreciated that all features and options mentioned in view of the method apply equally to the system and the computer program product.

BRIEF DESCRIPTION OF THE DRAWINGS

Embodiments of the present invention will now be described in detail with reference to the accompanying drawings in which.

DETAILED DESCRIPTION

Left bundle branch block (LBBB) after a transcatheter aortic valve implantation (TAVI) procedure is a frequent complication. LBBB after TAVI may occur in as much as 20 to 50% patients. This can result in increased mortality after one year. The underlying cause is to date still subject of speculation. Using the present technology, however, a predictor for the occurrence of LBBB or other conduction abnormalities can be given.

Figure 1:
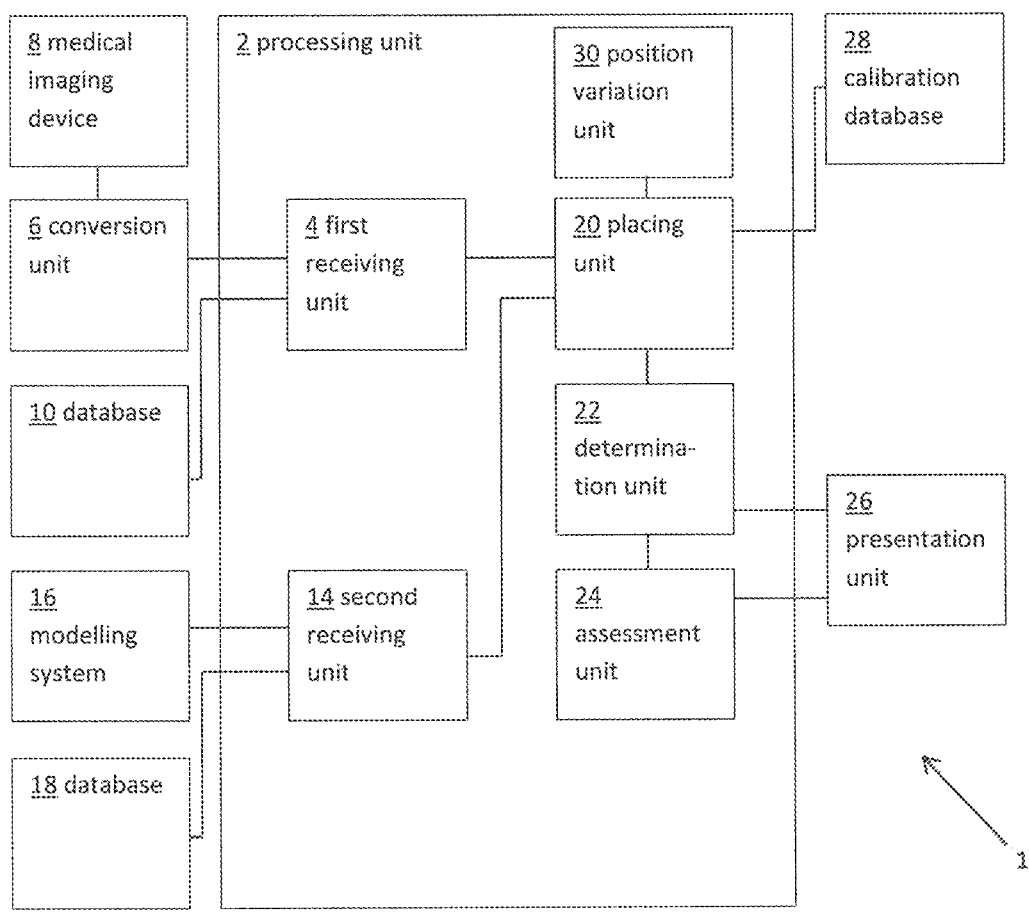
FIG. 1 is schematic representation of a system.

FIG. 1 shows a schematic example of a system 1 for determining a measure of a risk of a patient developing cardiac conduction abnormalities as a result of transcatheter cardiac valve treatment. The system includes a processing unit 2. The processing unit 2 includes a first receiving unit 4 for receiving a patient-specific anatomical model. Here the patient-specific anatomical model represents a patient-specific cardiac valve region. In this example, the patient-specific anatomical model is provided as a three dimensional (3D) finite element model comprising a finite element mesh. In this example the patient-specific anatomical model is received from a conversion unit 6. The conversion unit 6 is arranged for receiving medical imaging data from a medical imaging device 8. The medical imaging data may be 2D, 2.5D (stacked 2D) or 3D imaging data. The medical imaging data may be preoperative imaging data. The medical imaging device 8 may e.g. be a computer tomography (CT) device, an echocardiography device or a magnetic resonance imaging (MRI) device. In this example, the conversion unit 6 is arranged for creating the patient-specific 3D finite element model on the basis of the medical imaging data. Alternatively, or additionally, the patient-specific anatomical model can be received from a database 10.

The processing unit 2 further includes a second receiving unit 14 arranged for receiving an implant model representing a finite element representation of a cardiac valve implant. The finite element representation of the cardiac valve implant may e.g. be received from a 3D modelling system 16. Alternatively, or additionally, the finite element representation of the cardiac valve implant can be received from a database 18.

The processing unit 2 includes a placing unit 20 arranged for virtually placing said implant model into said patient-specific anatomical model. The placing unit 20 can be arranged for bringing the implant model and the patient-specific anatomical model in a common model space. The placing unit 20 can apply three dimensional finite element analysis. The placing by the placing unit also includes virtually expanding the implant model into the patient-specific anatomical model. The expanded implant model will abut against the patient-specific anatomical model. It will be appreciated that physical properties, such as stiffness, associated with both the implant model and the patient-specific anatomical model will determine the shape of the expanded implant model and a mechanical interaction between the implant model and the patient-specific anatomical model. The mechanical interaction includes force, pressure, stress, and strain between the implant model and the patient-specific anatomical model.

The processing unit 2 further includes a determination unit 22 arranged for determining, from the virtually placed implant model into said patient-specific anatomical model, a measure of the mechanical interaction between the implant model and the patient-specific anatomical model. In this example the determination unit 22 is arranged for determining a force exerted by the deployed implant model onto the patient-specific anatomical model and/or vice versa. Thereto the determination unit 22 can determine the deformation of the implant model and the patient-specific anatomical model due to deployment, and possible post-dilation. The deformations of both models, in conjunction with modeled elasticities of the models, allow to determine the force exerted by the one model onto the other. The elasticities of the models can be modeled as stiffnesses between nodes of the respective models. It will be appreciated that the force, when calculated on a node level amounts to a contact pressure over the surface area associated with that node.

Alternatively, or additionally, the determination unit 22 can determine a strain in tissue of the patient-specific anatomical model. The strain can be modeled as a force between adjacent nodes of the patient-specific anatomical model. Therefore, the measure of mechanical interaction can be a calculated quantification of a force and/or pressure exerted by the implant model onto the patient-specific anatomical model or vice versa. Alternatively, or additionally, the measure of mechanical interaction can be a calculated quantification of a strain in the tissue modelled by the patient-specific anatomical model.

The processing unit 2 further includes an assessment unit 24 arranged for determining a measure of risk of the patient developing cardiac conduction abnormalities on the basis of the determined mechanical interaction. The determined risk can e.g. be expressed as a percentage, a number, a level or the like. The processing unit 2 is communicatively connectable to a presentation unit 26. The presentation unit 26 in this example is a display to display the measure of risk of the patient developing cardiac conduction abnormalities on the basis of the determined mechanical interaction to a user. It will be appreciated that the presentation unit can also present a representation, such as a graphical representation, of the mechanical interaction to the user. Alternative, or additional, presentation units could be used, such as a hardcopy printer, an email server, a message service, a speaker device, etc.

Figure 2:
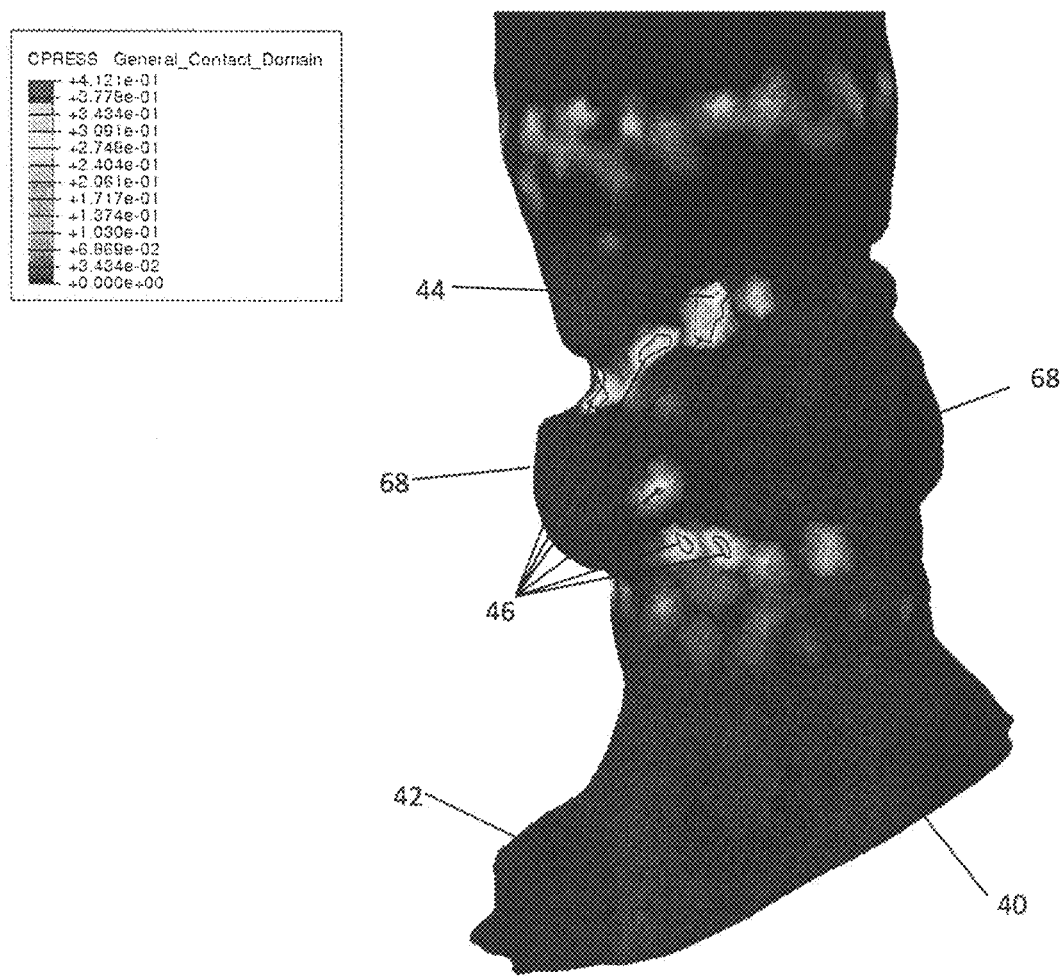
FIG. 2 is a first example in which a contact pressure between the implant model and the patient-specific anatomical model is represented.

FIG. 2 shows a first example in which a contact pressure between the implant model and the patient-specific anatomical model is represented. FIG. 2 shows a representation of an inner surface 40 of the aortic region of a patient-specific anatomical model. It is noted that the native valve leaflets 68 can be seen as pushed into the inner surface 40 of the aorta by the implant model. The determined value of the contact pressure is represented in false colors in this example, i.e. different colors represent different values of the contact pressure. In the example of FIG. 2 first areas 42 can be identified in which the contact pressure is zero. In the example of FIG. 2 second areas 44 can be identified in which the contact pressure is relatively high (approximately 0.4 N/mm² in this example). In this example the second areas extend just above, below and in between the native valve leaflets 68.

In the example of FIG. 2 a predetermined threshold contact pressure is defined. In the example of FIG. 2 third areas within which the contact pressure exceeds the exemplary threshold contact pressure are indicated with circumferential contour lines 46. Next, the determination unit 22 determines a total (cumulative) surface area within which the determined contact pressure exceeds the threshold. This surface area is representative for the risk of the patient developing cardiac conduction abnormalities.

Alternatively, or additionally, the determination unit 22 can determine a total contact force between the implant model and the patient-specific anatomical model. This total contact force is representative for the risk of the patient developing cardiac conduction abnormalities.

Alternatively, or additionally, the determination unit 22 can determine a peak contact force, i.e. a maximum contact force between the implant model and the patient-specific anatomical model. This peak force is representative for the risk of the patient developing cardiac conduction abnormalities.

Alternatively, or additionally, the determination unit 22 can determine a location in the patient-specific anatomical model where the peak force occurs. This location is representative for the risk of the patient developing cardiac conduction abnormalities.

It will be appreciated that the processing unit 2 may be arranged for applying a calibration. Thereto the processing unit 2 can include a calibration unit 28. Optionally, the measure of the mechanical interaction between the implant model and the patient-specific anatomical model is determined for a plurality of patients. For each of these patients the measure of mechanical interaction and the occurring or not-occurring of a conduction abnormality are stored in a calibration database. From this calibration database a correlation between the measure of mechanical interaction and the occurrence of a conduction abnormality can be determined. From the correlation a measure of risk of the patient developing cardiac conduction abnormalities on the basis of the determined mechanical interaction can be determined. It will be appreciated that the calibration database can be updated over time.

Figure 3:
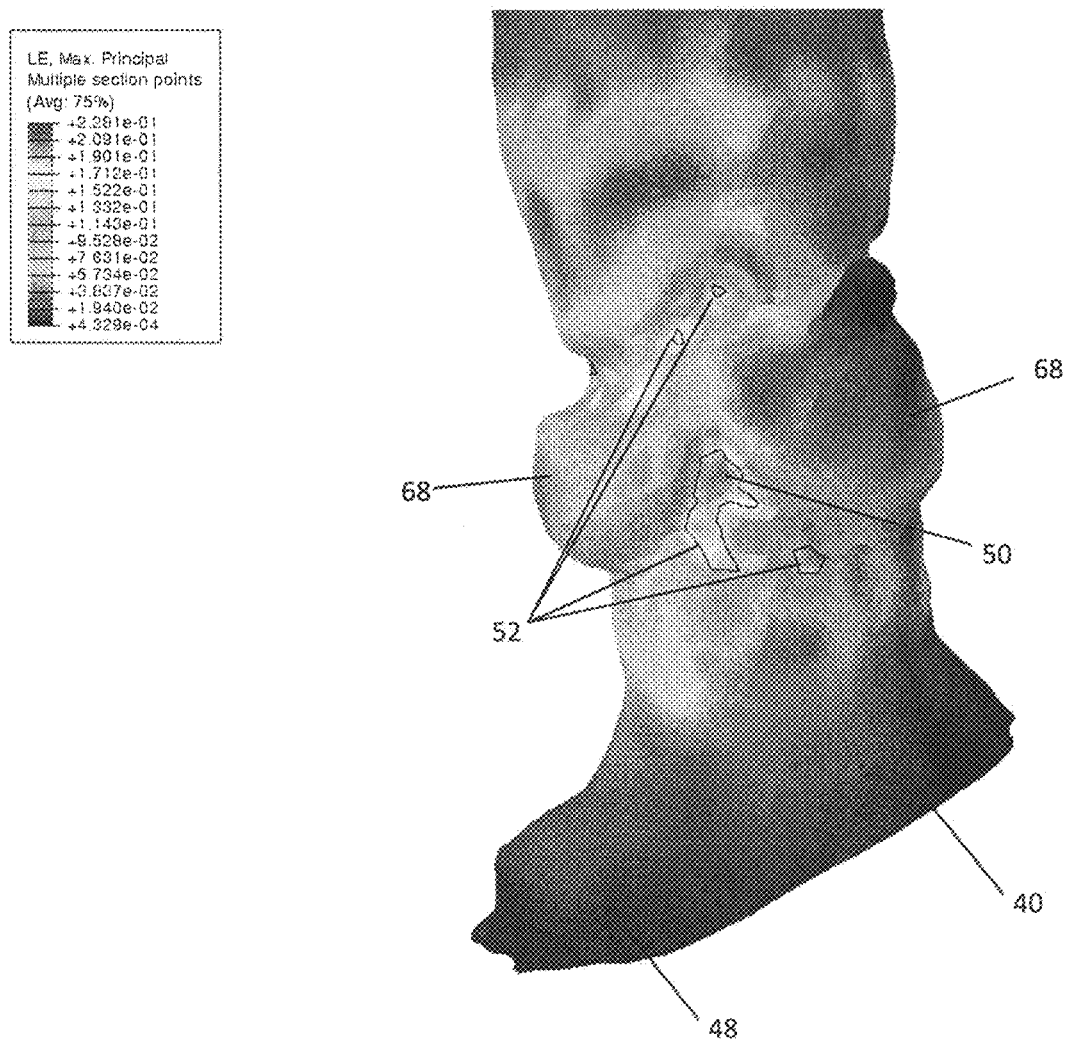
FIG. 3 is a second example in which a strain in the tissue of the patient-specific anatomical model is represented.

FIG. 3 shows a second example in which a strain in the tissue of the patient-specific anatomical model is represented. FIG. 3 shows a representation of an inner surface 40 of the aortic region of a patient-specific anatomical model. It is noted that the native valve leaflets 68 can be seen as pushed into the inner surface 40 of the aorta by the implant model. The determined value of the strain is represented in false colors in this example. In the example of FIG. 3 first areas 48 can be identified in which the strain is relatively low. In the example of FIG. 3 second areas 50 can be identified in which the strain is relatively high. In this example the second areas extend just above, below and in between the native valve leaflets 68.

In the example of FIG. 3 a predetermined threshold strain is defined. In the example of FIG. 3 third areas within which the strain exceeds the exemplary threshold strain are indicated with circumferential contour lines 52. Next, the determination unit 22 determines a total (cumulative) surface area within which the determined strain exceeds the threshold. This surface area is representative for the risk of the patient developing cardiac conduction abnormalities.

Alternatively, or additionally, the determination unit 22 can determine a total strain in the patient-specific anatomical model. This total strain is representative for the risk of the patient developing cardiac conduction abnormalities.

Alternatively, or additionally, the determination unit 22 can determine a peak strain, i.e. a maximum strain in the patient-specific anatomical model. This peak strain is representative for the risk of the patient developing cardiac conduction abnormalities.

Alternatively, or additionally, the determination unit 22 can determine a location in the patient-specific anatomical model where the peak strain occurs. This location is representative for the risk of the patient developing cardiac conduction abnormalities.

It will be appreciated that the calibration database 28 can include for each patient a plurality of measures of mechanical interaction such as peak force, total force, peak strain, surface area, etc. as described above.

Figure 4:
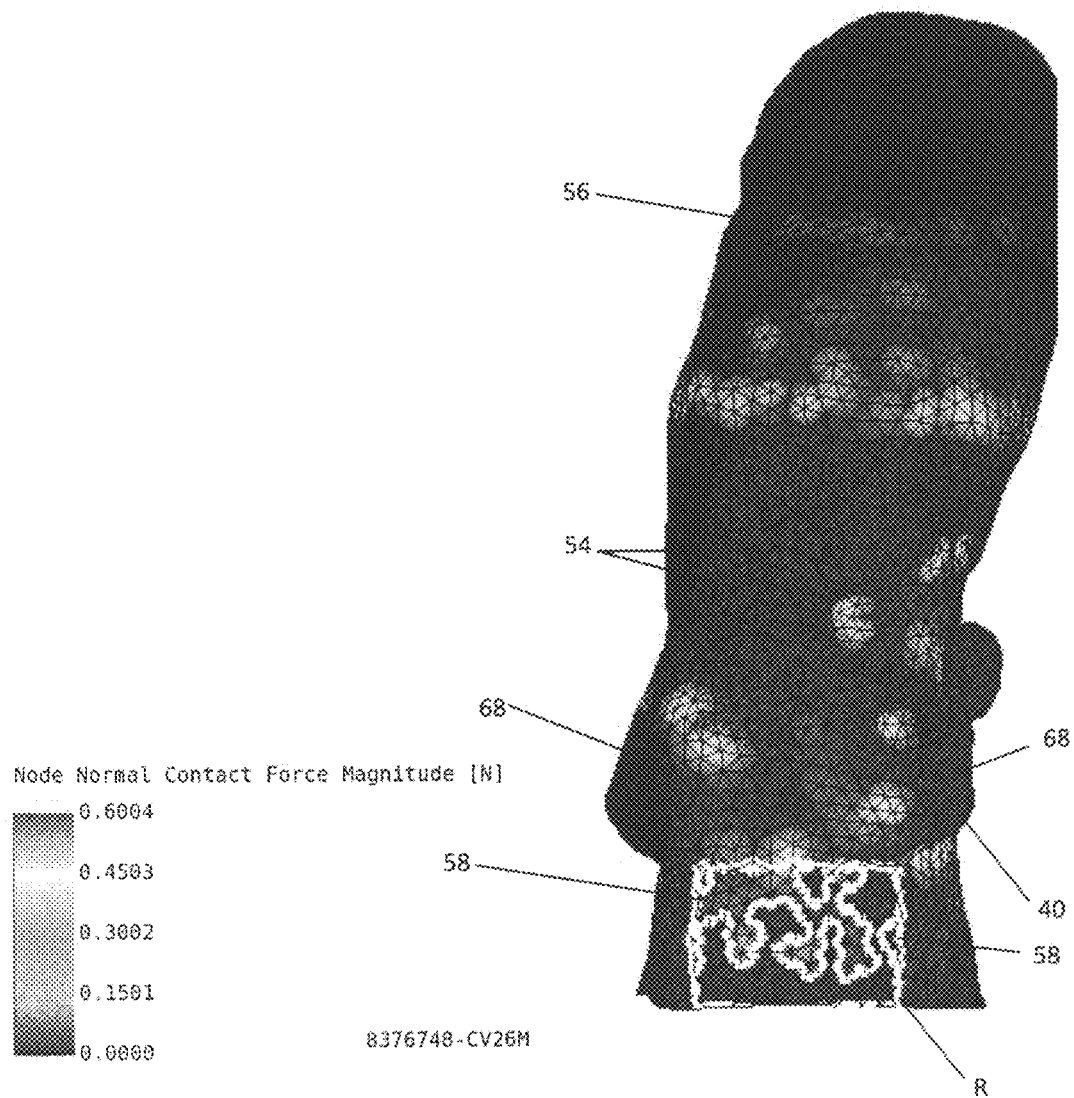
FIG. 4 is a third example in which a predetermined region R is defined in the patient-specific anatomical model.

FIG. 4 shows a representation of an inner surface 40 of the aortic region of a patient-specific anatomical model. In FIG. 4 the nodes 54 of the mesh 56 can be identified. FIG. 4 shows a third example in which a predetermined region R is defined in the patient-specific anatomical model. In this example, the predetermined region R is a part of the left ventricular outflow tract under the aortic annulus, between the basal attachment points of the non- and right coronary leaflet. In this example the predetermined region is a rectangular projection onto the patient-specific anatomical model. It will be appreciated that other shapes, such as triangular, circular, polygonal, or annular regions can also be used.

In FIG. 4 the contact pressure between the implant model and the patient-specific anatomical model is represented. The determined value of the contact pressure is represented in false colors in this example. In the example of FIG. 4 only the contact pressure within the predetermined region R is taken into account by the determination unit 22 or assessment unit 24.

As described with respect to FIG. 2 above, the determination unit 22 can for example determine within the predetermined region R a total surface area within which the determined contact pressure exceeds the threshold, a total contact force, a peak contact, and/or a location where the peak force occurs. These parameters are representative for the risk of the patient developing cardiac conduction abnormalities. It will be appreciated that similarly a predetermined region can be used in conjunction with determining strain. In the example of FIG. 4 within the predetermined region R third areas 58 within which the contact force exceeds the exemplary threshold contact force are indicated. In the example of FIG. 4 within the predetermined region R fourth areas 60 within which the contact force does not exceed the exemplary threshold contact force are indicated.

From the determined measure of the risk of the patient developing cardiac conduction abnormalities the user, e.g. an interventional cardiologist, can preoperatively assess the risk of cardiac conduction abnormalities arising from the projected TAVI or TAVR procedure. Using this risk assessment, an alternative procedure may be contemplated when the risk of the patient developing cardiac conduction abnormalities as a result of the TAVI or TAVR procedure are deemed too high. Alternatively, precautionary implantation of a pacemaker may be considered if the risk is high.

Figure 5A:
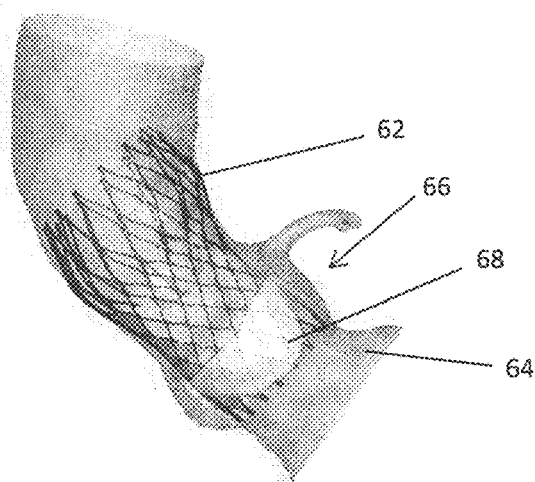
FIGS. 5a, 5b and 5c are an example wherein the implant model is deployed into the patient-specific anatomical model at a plurality of different locations.
Figure 5B:
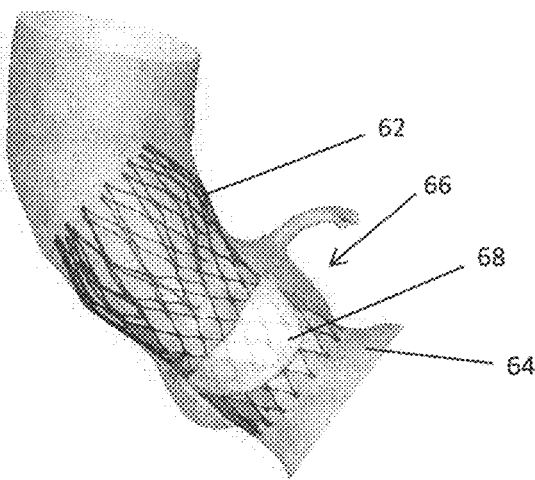
Figure 5C:
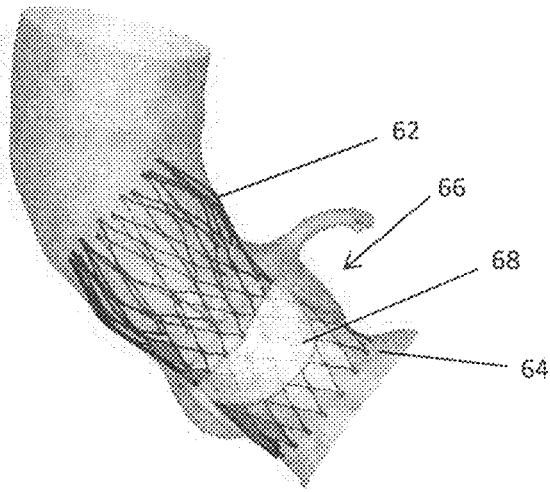

FIGS. 5*a*, 5*b* and 5*c* show an example wherein the implant model 62 is placed into the patient-specific anatomical model 64 at a plurality of different locations. In this example the patient-specific anatomical model 64 includes the region around the aortic valve 66. The native valve leaflets 68 can be identified in the FIGS. 5*a*-5*c*. In this example going from FIGS. 5*a* to 5*b* to 5*c* the implant model is placed at three positions which are successively shifted by three millimeters along the aortic root. Thereto the processing unit 2 includes a position variation unit 30. The assessment unit 24 determines the measure of the risk of the patient developing cardiac conduction abnormalities for each of the different locations. From this analysis a user can learn which position of the implant provides the lowest risk of the patient developing cardiac conduction abnormalities. This information can be used in planning of the TAVI or TAVR procedure.

It will be appreciated that it is also possible that a plurality of different implant models is provided. Each implant model can represent geometrical and/or material properties of a corresponding real-life implant. The implant models may e.g. differ in size, brand, construction, material or the like. Each of the implant models can then be placed into the patient specific anatomical model. The measure of the risk of the patient developing cardiac conduction abnormalities is then determined for each of the implant models. From this analysis it can be determined which one of the plurality of implant models has associated therewith the lowest risk of the patient developing cardiac conduction abnormalities. A cardiac valve implant corresponding to the implant model having the lowest associated risk of the patient developing cardiac conduction abnormalities can then be selected for a real-life percutaneous implantation procedure.

Figure 6A:
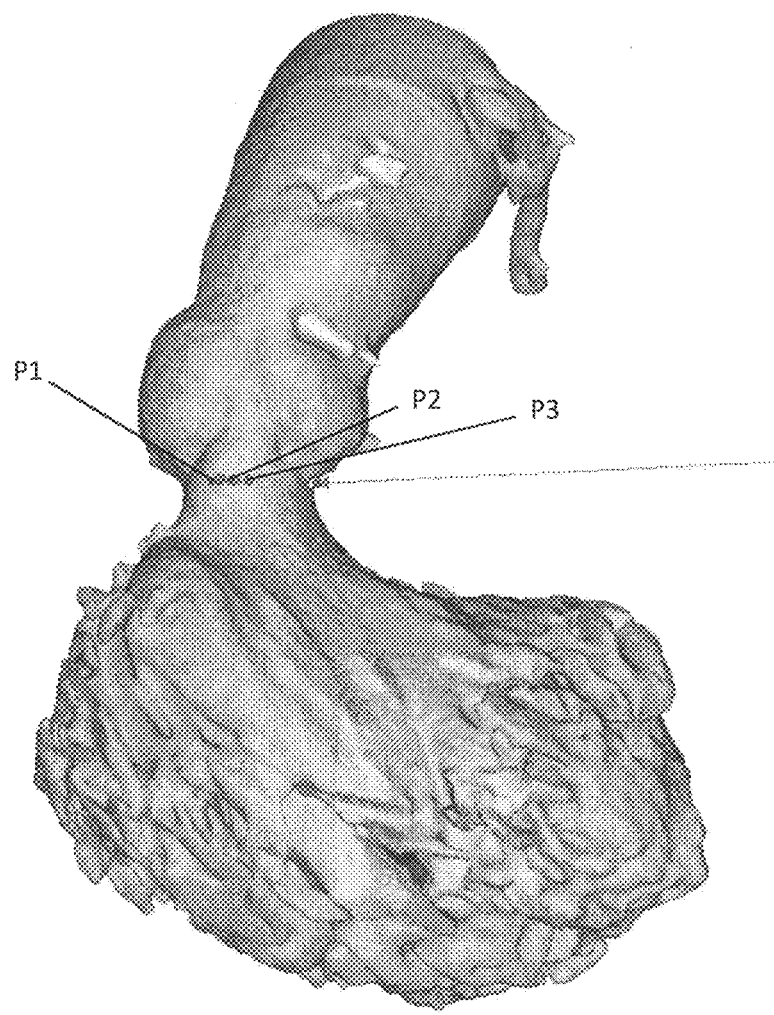
FIG. 6a is an example of a patient-specific anatomical model.
Figure 6B:
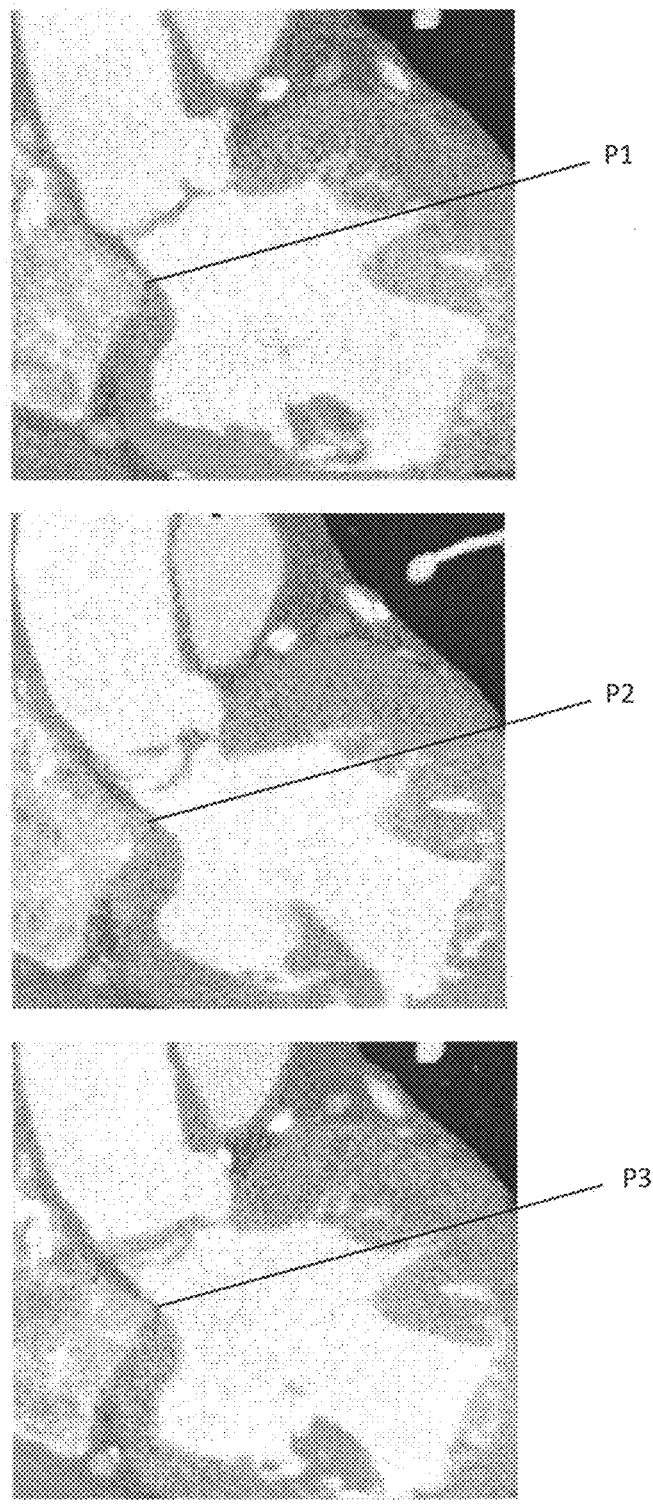
FIG. 6b shows three exemplary CT images.

FIG. 6a shows an example of a patient-specific model in which the location of the conduction system is indicated. The location of the conduction system is estimated from the location of the membranous septum as found in CT images. Here, the location of the conduction system is estimated from the position of three points in the CT images shown in FIG. 6b. A first point (p1) represents the starting point of the inferior margin closest to the non-coronary cusp, A third point (p3) represents the end of the inferior margin closest to the right coronary cusp. A third point (p2) is identified between the first and second points. The three points determine the estimated location of the conduction system in the patient specific anatomical model shown in FIG. 6a. It is noted that there can be a large variation in location of the inferior margin of the membranous septum from patient to patient. Therefore, providing the estimated location of the conduction system obtained from patient-specific data on the location of the membranous septum can greatly enhance accuracy estimating any effects of mechanical interaction between the implant model and the patient-specific model.

It will be appreciated that it is possible to determine the measure of the mechanical interaction includes determining the measure of mechanical interaction at or around the estimated location of the conduction system. It is possible to determine measure of contact pressure, or a measure of strain in the tissue of the patient-specific anatomical model at the estimated location of the conduction system, e.g. at a band (e.g. of predetermined width) from point p1 to p2 to p3. It is possible to determine a measure of a surface area within which the determined mechanical interaction exceeds a predetermined threshold at the estimated location of the conduction system, e.g. in a band (e.g. of predetermined width) from point p1 to p2 to p3. It is possible to determine a total contact force at the estimated location of the conduction system, e.g. in a band (e.g. of predetermined width) from point p1 to p2 to p3. It is possible to determine a peak pressure of the contact pressure at the estimated location of the conduction system, e.g. in a band (e.g. of predetermined width) from point p1 to p2 to p3. It is possible to determine a location in the patient-specific anatomical model where the peak pressure occurs at the estimated location of the conduction system, e.g. in a band (e.g. of predetermined width) from point p1 to p2 to p3.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

It will be appreciated that in each of the examples, and in general, determining the measure of the mechanical interaction may include determining a plurality of situations of progressing deployment of the implant model into the patient-specific anatomical model. The situations may progressively differ by a predetermined amount or ratio of deployment. The deployment can include insertion of the implant model into the patient-specific anatomical model. The insertion can include travel of a model of a, collapsed, implant along a vessel. The situations can include progressively differing positions of insertion up to the intended deployment position. The deployment can include expansion of the implant model in the patient-specific anatomical model. The situations can include progressively differing stages of expansion of the implant model. For each of the situations the measure of the mechanical interaction can be determined as described above. Hence, all stages of deployment can be modeled. The processing unit may be arranged to determine the situation of the plurality of situations in which the determined mechanical interaction is most significant, e.g. highest. The processing unit may be arranged to determine the measure of mechanical interaction in the situation of the plurality of situations in which the determined mechanical interaction is most significant for predicting conduction problems, e.g. highest.

It will be appreciated that such determining of a plurality of situations simulates determining an evolution of the measure of the mechanical interaction between the implant model and the patient-specific anatomical model over time during the process of deployment. It will be appreciated that the processing unit, first receiving unit, conversion unit, second receiving unit, modelling system, placing unit, determination unit, assessment unit, presentation unit, and/or position variation unit can be embodied as dedicated electronic circuits, possibly including software code portions. The processing unit, first receiving unit, conversion unit, second receiving unit, modelling system, placing unit, determination unit, assessment unit, presentation unit, and/or position variation unit can also be embodied as software code portions executed on, and e.g. stored in, a memory of, a programmable apparatus such as a computer, tablet or smartphone.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means, e.g. via the internet or cloud.

When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference sign placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A method for determining a measure of a risk of a patient developing cardiac conduction abnormalities as a result of transcatheter structural heart intervention, the method comprising:
providing a patient-specific anatomical model representing a patient-specific cardiac region, the patient-specific anatomical model comprising a finite element mesh;
providing an implant model representing a finite element representation of a cardiac implant;
virtually placing the implant model into the patient-specific anatomical model;
determining, from the virtually placed implant model into the patient-specific anatomical model, a measure of mechanical interaction between the implant model and the patient-specific anatomical model; and
determining a measure of risk of the patient developing cardiac conduction abnormalities on the basis of the determined mechanical interaction,
wherein the virtually placing and the determining the measure of risk comprise virtually placing the implant model into the patient-specific anatomical model at a plurality of different locations and determining the measure of the risk of the patient developing cardiac conduction abnormalities for each of the different locations.

2. The method of claim 1, wherein the measure of mechanical interaction is a measure of contact pressure, or a measure of strain in the tissue of the patient-specific anatomical model.

3. The method of claim 2, wherein determining the measure of the mechanical interaction includes: determining a peak pressure of the contact pressure.

4. The method of claim 3, wherein determining the measure of the mechanical interaction includes:
determining a location in the patient-specific anatomical model where the peak pressure occurs.

5. The method of claim 2, further including displaying the measure of the contact pressure on a display.

6. The method of claim 1, wherein determining the measure of the mechanical interaction includes: determining a measure of a surface area within which the determined mechanical interaction exceeds a predetermined threshold.

7. The method of claim 1, wherein determining the measure of the mechanical interaction includes: determining a total contact force.

8. The method of claim 1, wherein determining the measure of the mechanical interaction includes:
defining a predetermined region of the patient-specific anatomical model, and
determining the measure of the mechanical interaction within that predetermined region.

9. The method of claim 1, wherein determining the measure of the mechanical interaction includes:
determining an evolution of the mechanical interaction over time.

10. The method of claim 1, wherein the implant model comprises a finite element mesh wherein each element of a mesh of the finite element mesh is featured by a set of nodes wherein adjacent elements of the element comprise mutually shared nodes with the element, wherein the element is featured by material dependent parameters and wherein each element of the mesh can differ in material dependent parameters from an adjacent element of the element of the mesh.

11. The method of claim 1, wherein the step of virtually placing the implant model into the patient-specific anatomical model comprises applying a three-dimensional finite element analysis.

12. The method of claim 1, wherein the step of virtually placing the implant model includes:
providing a plurality of implant models, each comprising geometrical and/or material properties of a corresponding implant; and
virtually placing each of the implant models into the patient specific anatomical model, and determining the measure of the risk of a patient developing cardiac conduction abnormalities for each of the implant models.

13. The method of claim 12, including selecting a cardiac implant corresponding to one of the plurality of the implant models for a percutaneous implantation procedure.

14. The method of claim 1, wherein the transcatheter structural heart intervention is a transcatheter cardiac valve treatment, wherein the patient-specific anatomical model represents a patient-specific cardiac valve region, and wherein the implant model represents a finite element representation of a cardiac valve implant.

15. A method for determining a measure of a risk of a patient developing cardiac conduction abnormalities as a result of transcatheter structural heart intervention, the method comprising:
providing a patient-specific anatomical model representing a patient-specific cardiac region, the patient-specific anatomical model comprising a finite element mesh;
providing an implant model representing a finite element representation of a cardiac implant;
virtually placing the implant model into the patient-specific anatomical model;
determining, from the virtually placed implant model into the patient-specific anatomical model, a measure of mechanical interaction between the implant model and the patient-specific anatomical model;
determining a measure of risk of the patient developing cardiac conduction abnormalities on the basis of the determined mechanical interaction; and
estimating a position of a conduction system in the patient-specific anatomical model.

16. The method of claim 15, wherein determining the measure of the mechanical interaction includes:
determining the measure of mechanical interaction at or around the estimated position of the conduction system.

17. A system for determining a measure of a risk of a patient developing cardiac conduction abnormalities as a result of transcatheter structural heart intervention, the system comprising a processor, the system configured to:
receive a patient-specific anatomical model representing a patient-specific cardiac region, the patient-specific anatomical model comprising a finite element mesh;
receive an implant model representing a finite element representation of a cardiac implant;
virtually place the implant model into the patient-specific anatomical model;
determine, from the virtually placed implant model into the patient-specific anatomical model, a measure of a mechanical interaction between the implant model and the patient-specific anatomical model; and determine a measure of risk of the patient developing cardiac conduction abnormalities on the basis of the determined mechanical interaction, wherein to virtually place and to determine the measure of risk comprise virtually place the implant model into the patient-specific anatomical model at a plurality of different locations and determine the measure of the risk of the patient developing cardiac conduction abnormalities for each of the different locations.

18. A non-transient computer-readable medium comprising computer implementable instructions which when implemented by a programmable computer cause the computer to:

retrieve a patient-specific anatomical model representing a patient-specific cardiac region, the patient-specific anatomical model comprising a finite element mesh;

retrieve an implant model representing a finite element representation of a cardiac implant;

virtually place the implant model into the patient-specific anatomical model;

determine, from the virtually placed implant model into the patient-specific anatomical model, a measure of a mechanical interaction between the implant model and the patient-specific anatomical model; and determine a measure of risk of the patient developing cardiac conduction abnormalities on the basis of the determined mechanical interaction, wherein to virtually place and to determine the measure of risk comprise virtually place the implant model into the patient-specific anatomical model at a plurality of different locations and determine the measure of the risk of the patient developing cardiac conduction abnormalities for each of the different locations.

19. A system for determining a measure of a risk of a patient developing cardiac conduction abnormalities as a result of transcatheter structural heart intervention, the system comprising a processor, the system configured to:

retrieve a patient-specific anatomical model representing a patient-specific cardiac region, the patient-specific anatomical model comprising a finite element mesh;

retrieve an implant model representing a finite element representation of a cardiac implant;

virtually place the implant model into the patient-specific anatomical model;

determine, from the virtually placed implant model into the patient-specific anatomical model, a measure of mechanical interaction between the implant model and the patient-specific anatomical model;

determine a measure of risk of the patient developing cardiac conduction abnormalities on the basis of the determined mechanical interaction; and estimate a position of a conduction system in the patient-specific anatomical model.

20. A non-transient computer-readable medium comprising computer implementable instructions which when implemented by a programmable computer cause the computer to:

retrieve a patient-specific anatomical model representing a patient-specific cardiac region, the patient-specific anatomical model comprising a finite element mesh;

retrieve an implant model representing a finite element representation of a cardiac implant;

virtually place the implant model into the patient-specific anatomical model;

determine, from the virtually placed implant model into the patient-specific anatomical model, a measure of mechanical interaction between the implant model and the patient-specific anatomical model;

determine a measure of risk of the patient developing cardiac conduction abnormalities on the basis of the determined mechanical interaction; and estimate a position of a conduction system in the patient-specific anatomical model.

* * * * *